(12) United States Patent
Choi et al.

(10) Patent No.: US 11,666,390 B2
(45) Date of Patent: Jun. 6, 2023

(54) SYSTEM AND METHOD FOR PLANNING PEDICLE SCREW FIXATION

(71) Applicant: CUREXO, INC., Seoul (KR)

(72) Inventors: Jin Hyeok Choi, Gwangju-si (KR); Dong Gi Woo, Seoul (KR); Sung Teac Hwang, Seoul (KR); Seong Yi, Seoul (KR)

(73) Assignee: CUREXO, INC., Seoul (KR)

( * ) Notice: Subject to any disclaimer, the term of this patent is extended or adjusted under 35 U.S.C. 154(b) by 1 day.

(21) Appl. No.: 17/437,713

(22) PCT Filed: Mar. 13, 2020

(86) PCT No.: PCT/KR2020/003565
§ 371 (c)(1),
(2) Date: Sep. 9, 2021

(87) PCT Pub. No.: WO2020/185049
PCT Pub. Date: Sep. 17, 2020

(65) Prior Publication Data
US 2022/0039875 A1 Feb. 10, 2022

(30) Foreign Application Priority Data

Mar. 13, 2019 (KR) .......................... 10-2019-0028981

(51) Int. Cl.
*A61B 34/20* (2016.01)
*A61B 34/10* (2016.01)
(Continued)

(52) U.S. Cl.
CPC .......... *A61B 34/20* (2016.02); *A61B 17/7082* (2013.01); *A61B 34/10* (2016.02);
(Continued)

(58) Field of Classification Search
CPC ..... A61B 34/20; A61B 17/7082; A61B 34/10; A61B 34/25; A61B 90/37;
(Continued)

(56) References Cited

U.S. PATENT DOCUMENTS 6,226,548 B1 5/2001 Clayton et al.
6,285,902 B1 9/2001 Kienzle, III et al.
(Continued)

FOREIGN PATENT DOCUMENTS

EP 3306567 A1 4/2018
JP 2005-525858 A 9/2005
(Continued)

*Primary Examiner* — Christopher L Cook
(74) *Attorney, Agent, or Firm* — Bridgeway IP Law Group, PLLC; Jihun Kim

(57) ABSTRACT

A system for planning pedicle screw fixation includes: a C-arm configured to capture a spinal image of a patient; an insertion path provider configured to provide an entry point and an insertion endpoint of a pedicle screw on a C-arm image; a registrator configured to calculate spatial coordinates of the entry point and the insertion endpoint based on a reference coordinate system; a guider configured to determine an insertion position of the pedicle screw based on the spatial coordinates of the entry point and the insertion endpoint, and guide a probe to be inserted toward the entry point according to the insertion positions; and a screw determiner configured to determine a length condition of the pedicle screw by obtaining coordinates of a start point at which the probe is inserted and becomes in contact with a bone.

9 Claims, 14 Drawing Sheets

(51) Int. Cl.
*A61B 34/00* (2016.01)
*A61B 90/00* (2016.01)
*A61B 17/70* (2006.01)

(52) U.S. Cl.
CPC .............. *A61B 34/25* (2016.02); *A61B 90/37* (2016.02); *A61B 2034/105* (2016.02); *A61B 2034/2055* (2016.02); *A61B 2090/3764* (2016.02)

(58) Field of Classification Search
CPC .... A61B 2034/1005; A61B 2034/2055; A61B 2090/3764
See application file for complete search history.

(56) References Cited

U.S. PATENT DOCUMENTS

| | | |
|---|---|---|
| 2005/0149050 A1 | 7/2005 | Holger et al. |
| 2007/0270866 A1 | 11/2007 | von Jako |
| 2009/0124895 A1* | 5/2009 | Roden .................... A61B 6/12 600/427 |
| 2010/0100132 A1 | 4/2010 | Pacheco |
| 2010/0241129 A1* | 9/2010 | Markey ............. A61B 17/1757 606/104 |
| 2016/0038248 A1* | 2/2016 | Bharadwaj ............. A61B 90/10 715/771 |
| 2018/0256259 A1 | 9/2018 | Crawford |
| 2018/0325608 A1* | 11/2018 | Kang ................... A61B 34/32 |
| 2018/0333214 A1 | 11/2018 | Han et al. |
| 2021/0077047 A1* | 3/2021 | Tolkowsky ........... A61B 90/39 |

FOREIGN PATENT DOCUMENTS

| | | |
|---|---|---|
| KR | 10-2007-0045023 A | 5/2007 |
| KR | 10-1264198 B1 | 5/2013 |
| KR | 10-2017-0062048 A | 6/2017 |
| KR | 102203544 B1 | 1/2021 |

* cited by examiner

AP

SYSTEM AND METHOD FOR PLANNING PEDICLE SCREW FIXATION

TECHNICAL FIELD

The disclosure relates to a system and method for planning pedicle screw fixation, and more particularly to a system and method for planning the length, insertion path, etc. of a pedicle screw based on a C-arm image.

BACKGROUND ART

A pedicle screw is used for spinal fixation as inserted and fixed in a vertebral body through a pedicle, the pedicle screw fixation planning refers to a procedure in which a surgical operator determines the length, diameter, etc. of a pedicle screw suitable for a patient and a surgical site, and an insertion path of the pedicle screw is previously planned.

As shown in FIG. 1, an axial view of a spine is the most advantageous to a surgical operator's planning. However, a C-arm apparatus cannot provide the axial view of the spine, and therefore a computed tomography (CT) image is taken before surgery to provide the axial view to the surgical operator for the purpose of doing preoperative planning.

Although the CT image is used to perform the planning, a mobile C-arm X-ray apparatus is mostly used in an actual surgical procedure, and therefore registration between the CT image and a C-arm 2D image needs to take precedence so as to verify in real time whether surgery is carried out as planned preoperatively or to navigate a surgical tool as planned. Further, the registration needs to be performed all over again if a patient moves or the C-arm apparatus moves.

The CT-image-based planning the has advantages of providing the axial view as above, but disadvantages that a CT scan is harmful to a human body due to prolonged radiation exposure and the registration with the C-arm 2D image is required.

On the other hand, the C-arm image does not provide the axial view of the spine and is not suitable for the planning because a spinal part needed for the planning is not fully shown on an anterior-posterior (AP) image and a lateral-lateral (LL) image.

Although the planning is not practically performed based on the C-arm image, a C-arm is the apparatus being used in the surgical procedure. Accordingly, if the planning is performed based on the C-arm image, there are many advantages that the registration between the 3D CT image and the 2D image is not required, surgical planning is flexibly modifiable as necessary even during surgery, etc.

DISCLOSURE

Technical Problem

Accordingly, the disclosure is conceived to solve the foregoing problems of the related art, and an aspect of the disclosure is to provide a planning system and method in which pedicle screw fixation planning is possible based on a C-arm image.

Technical Solution

According to an aspect of the disclosure, there is provided a system for planning pedicle screw fixation, including: a C-arm configured to capture a spinal image of a patient; an insertion path provider configured to provide an entry point and an insertion endpoint of a pedicle screw on a C-arm image; a registrator configured to calculate spatial coordinates of the entry point and the insertion endpoint based on a reference coordinate system; a guider configured to determine an insertion position of the pedicle screw based on the spatial coordinates of the entry point and the insertion endpoint, and guide a probe to be inserted toward the entry point according to the insertion positions; and a screw determiner configured to determine a length condition of the pedicle screw by obtaining coordinates of a start point at which the probe is inserted and becomes in contact with a bone, and calculating a distance between the coordinates of the insertion end point and the coordinates of the start point.

Here, the entry point may be determined at a certain point on a line connecting the insertion end point and a center of a pedicle on an anterior-posterior (AP) image, or may be determined at a certain point on a line extended from the insertion endpoint in parallel with a horizontal line of a vertebral body on a lateral-lateral (LL) image.

The system for planning pedicle screw fixation may further include an optical tracking device configured to track a location of the probe to which an optical marker is connected, wherein the registrator is configured to determine a pixel on the C-arm image to which the location of the probe is registered, and the insertion path provider is configured to display a projected image of the probe on the registered pixels.

Further, the insertion path provider may include a user interface allowing a surgical operator to select the entry point and the insertion endpoint on the C-arm image.

According to another aspect of the disclosure, there is provided a method of planning pedicle screw fixation, including: (a) obtaining a C-arm image of a spine of a patient through a C-arm; (b) determining an entry point and an insertion endpoint of a pedicle screw on the C-arm image; (c) calculating spatial coordinates of the entry point and the insertion endpoint based on a reference coordinate system; (d) determining an insertion position of the pedicle screw based on the spatial coordinates of the entry point and the insertion endpoint, and guiding a probe to be inserted toward the entry point according to the insertion positions; (e) obtaining coordinates of a start point at which the probe is inserted and becomes in contact with a bone based on the reference coordinate system; and (f) determining a length condition of the pedicle screw by calculating a distance between the coordinates of the insertion end point and the coordinates of the start point.

Here, the entry point in the (b) may be determined at a certain point on a line connecting the insertion end point and a center of a pedicle on an anterior-posterior (AP) image, or may be determined at a certain point on a line extended from the insertion endpoint in parallel with a horizontal line of a vertebral body on a lateral-lateral (LL) image.

Further, in the (b), a surgical operator may select the entry point and the insertion endpoint on the C-arm image through a user interface.

Advantageous Effects

According to the disclosure, a C-arm image is used instead of a CT image that has conventionally been used in planning, thereby reducing radiation exposure to a patient and simplifying a surgical procedure.

According to the disclosure, it is possible to modify and adjust surgical planning based on a C-arm image even during surgery, and it is possible to omit image registration, thereby reviewing surgical proceedings and improving accuracy in navigating a surgical tool. Further, a screw guide position used in planning is continuously usable for surgery, and it is thus possible to quickly carry out a surgical procedure.

MODE FOR INVENTION

Below, embodiments of the disclosure will be described with reference to the accompanying drawings.

Figure 1:
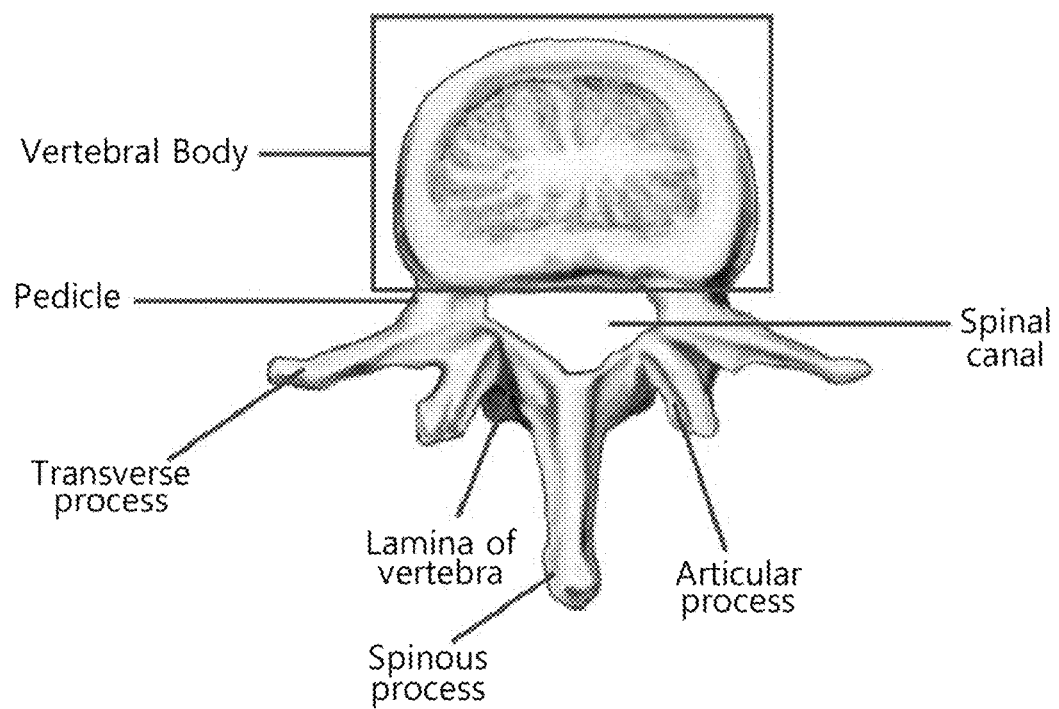
FIG. 1 illustrates an axial view of a spinal structure.
Figure 2:
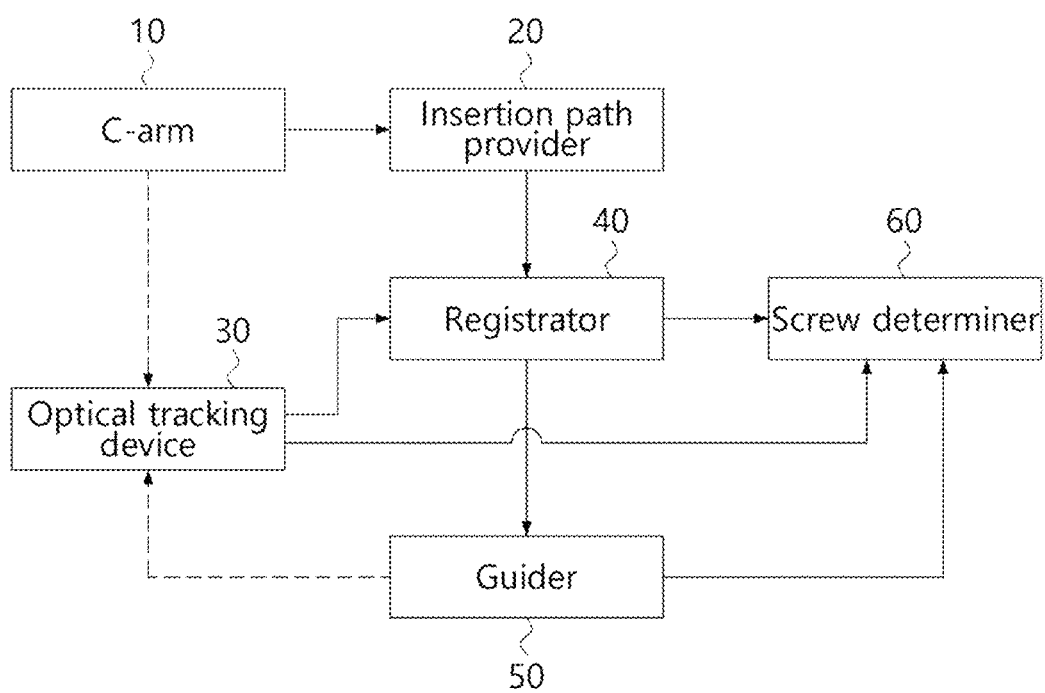
FIG. 2 is a schematic block diagram of a planning system for pedicle screw fixation according to an embodiment of the disclosure.

FIG. 2 is a schematic block diagram of a planning system for pedicle screw fixation according to an embodiment of the disclosure.

Referring to FIG. 2, the planning system for pedicle screw fixation according to an embodiment of the disclosure includes a C-arm 10, an insertion path provider 20, an optical tracking device 30, a registrator 40, a guider 50, and a screw determiner 60.

The C-arm 10 is to capture a spinal image of a patient, and uses an X-ray source and a detector, which are provided at opposite ends of a C-shaped frame, to capture a C-arm X-ray image.

The insertion path provider 20 is to provide an entry point and an insertion endpoint for a pedicle screw corresponding to the C-arm image. Here, the insertion endpoint refers to a location of a screw end when the pedicle screw is inserted and fixed in a pedicle body, and the entry point refers to a location selected to determine an insertion path of the pedicle screw based on a relative location relationship with the insertion endpoint.

Information about the entry point and the insertion endpoint may be provided by a clinical decision support system (CDSS) that automatically generates a recommendation location information based on a C-arm image. The CDSS may be established based on deep learning of the C-arm images, and may use artificial intelligence (AI) or medical explainable artificial intelligence (XAI) based on various deep learning algorithms such as a multi-layer perceptron (MLP), a convolutional neural network (CNN), etc.

Alternatively, the information about the entry point and the insertion endpoint may be determined as a surgical operator directly designates the entry point and the insertion endpoint on the C-arm image through a user interface (UI). The surgical operator, who has professional knowledge, may select the entry point and the insertion endpoint through the UI without help of the CDSS.

Further, the information about the entry point and the insertion endpoint may be provided based on standardized statistical criteria or the like of patients and surgical sites and then adjusted by a surgical operator who has professional knowledge. Like this, the information about the entry point and the insertion endpoint may be determined by various ways.

The optical tracking device 30 recognizes a reference marker (not shown) inside a surgical space and provides a reference coordinate system, thereby transforming locations of various devices and instruments installed with the optical markers into those in the reference coordinate system.

The registrator 40 is to calculate spatial coordinates of the entry point and the insertion endpoint in the reference coordinate system. In other words, the registrator 40 is to calculate spatial coordinates of locations inside a spine corresponding to the entry point and the insertion endpoint on the C-arm image.

Specifically, the registrator 40 may for example determine an intersection by back-projection along an X-ray path from the same entry point (or insertion endpoint) on a C-arm AP image and a C-arm LL image based on the spatial coordinates of the X-ray source and the detector of the C-arm when the C-arm AP image and the C-arm LL image are captured, thereby calculating the spatial coordinates. Here, the spatial coordinates of the X-ray source and the detector of the C-arm may be calculated by attaching the optical markers to the X-ray source and the detector. Here, the surface of the detector should be set on the same plane as the C-arm image.

If it is difficult to identify the locations of the X-ray source and the detector, the registration may be achieved based on the method disclosed in Korean Patent Application No. 2019-0028592, applied by the present applicant on Mar. 13, 2019 and titled 'C-ARM MEDICAL IMAGING SYSTEM AND REGISTRATION METHOD OF 2D IMAGE AND 3D SPACE.' In brief, the spatial coordinates are calculated in such a manner that an intersection is obtained from a plurality of images by warping an AP image on the surface of the detector to a third plane, and back-projecting pixels from a newly generated image to a space.

Referring back to FIG. 2, the guider 50 determines an insertion position of the pedicle screw based on the spatial coordinates of the entry point and the insertion endpoint, and guides insertion of a probe toward the entry point. The guider 50 may be embodied by an automatic or semiautomatic device or medical robot. A publicly-known medical robot automatically moves to a location for screw insertion by means of the optical tracking device 30 when only position coordinates are given, and controls positions of an end effector (not shown) and a guide jig so that the probe can be inserted according to insertion positions.

The screw determiner 60 obtains the coordinates of the start point at which the probe is inserted and becomes in contact with a bone. Here, an insertion depth of a probe end may be calculated based on the optical markers attached to the probe, the end effector (not shown) for transferring insertion force to the probe, or the like according to a probe insertion mechanism.

The screw determiner 60 determines a length condition of the pedicle screw by calculating a distance between the coordinates of the insertion endpoint and the coordinates of the start point. Here, the start point and the insertion endpoint indicate a total length of the pedicle screw to be inserted in a spine, and therefore the length condition of the pedicle screw may be determined to have a length from the start point to the insertion endpoint, or a length longer by a predetermined length than the length from the start point to the insertion endpoint.

Figure 3:
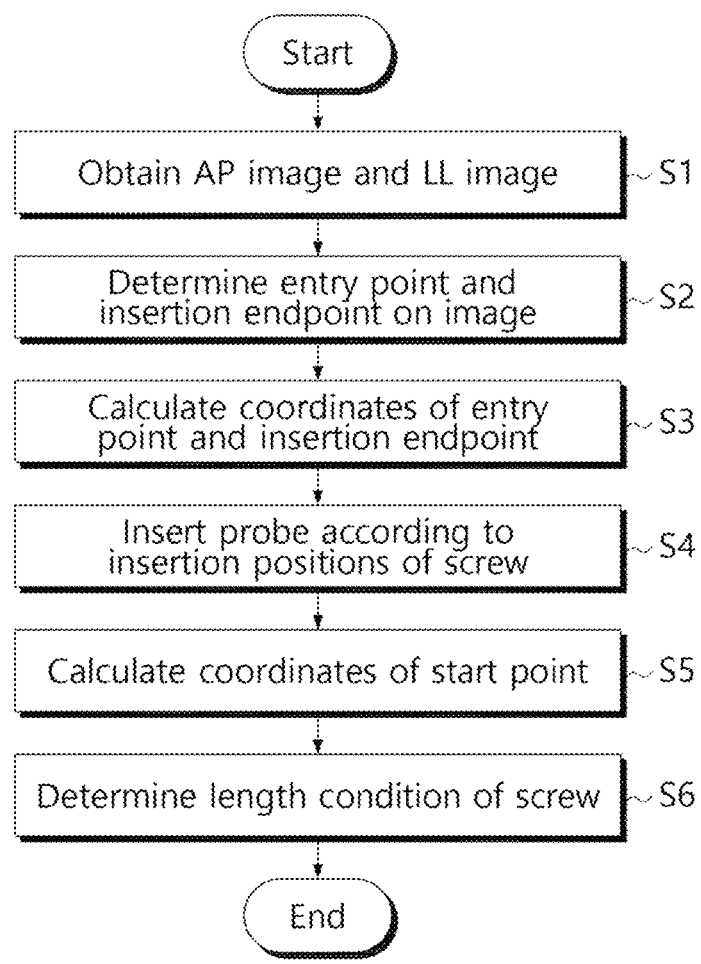
FIG. 3 is a flowchart of a planning method of the pedicle screw fixation according to an embodiment of the disclosure.

FIG. 3 is a flowchart of a planning method of the pedicle screw fixation according to an embodiment of the disclosure, and FIGS. 4A to 10B are schematic views for describing a process of planning the pedicle screw fixation according to an embodiment of the disclosure.

Referring to FIG. 3 to FIG. 10B, operations of the planning system for pedicle screw fixation according to an embodiment of the disclosure shown in FIG. 2 will be described.

Figure 4A:
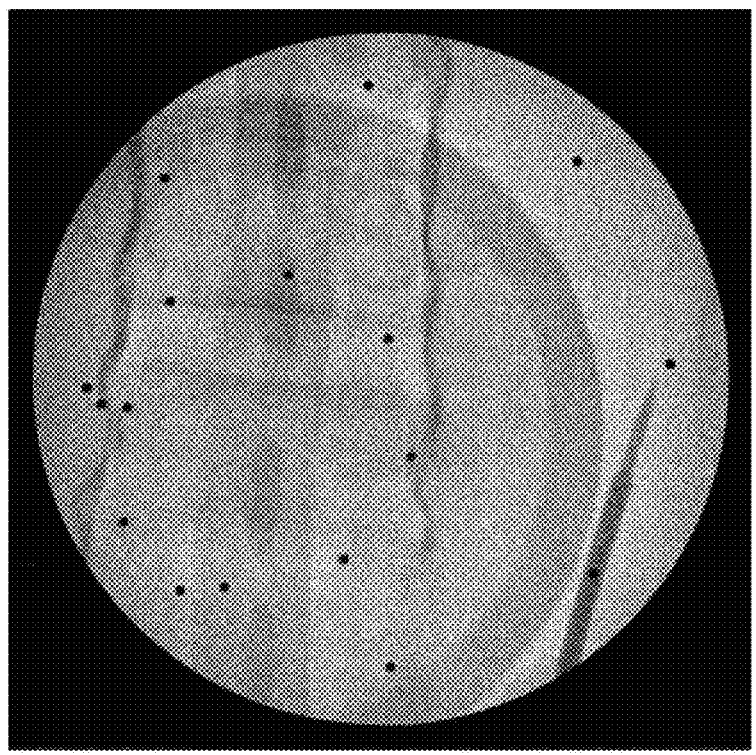
FIGS. 4A to 10B are schematic views for describing a process of planning the pedicle screw fixation according to an embodiment of the disclosure.
Figure 4B:
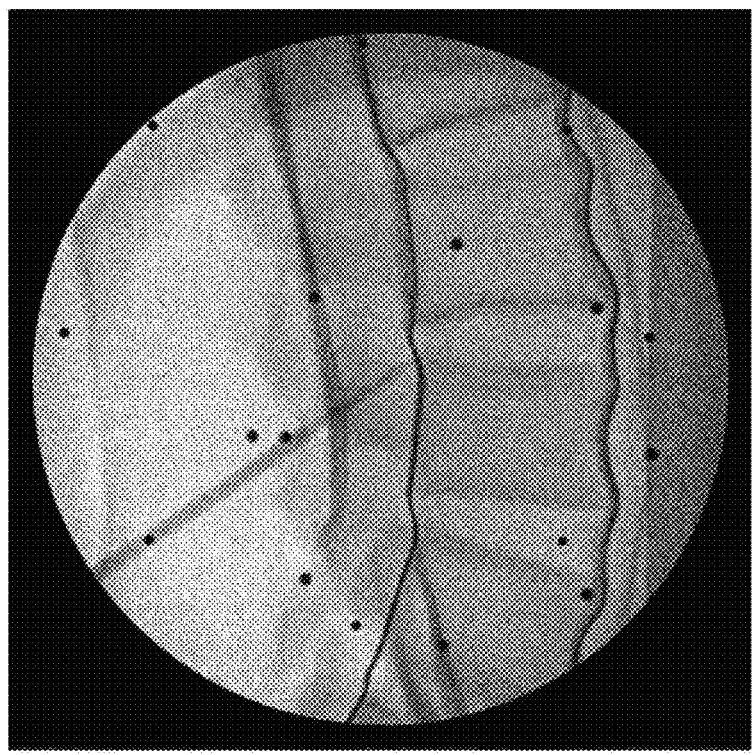

First, the C-arm 10 is used to obtain an AP image and an LL image of a patient's spine (S1). It is well known to a person having ordinary knowledge in the art that the C-arm 10 is used to capture the AP image and the LL image, and therefore detailed descriptions thereof will be omitted for simplicity and clarity of description. Thus, FIGS. 4A and 4B illustrate the AP image and the LL image for describing a planning process according to an embodiment of the disclosure.

The C-arm 10 provides the captured AP image and the captured LL image to the insertion path provider 20, and the insertion path provider 20 provides the insertion path for the pedicle screw or the probe by determining the entry point and the insertion endpoint of the pedicle screw on the AP image and the LL image (S2).

Figure 5A:
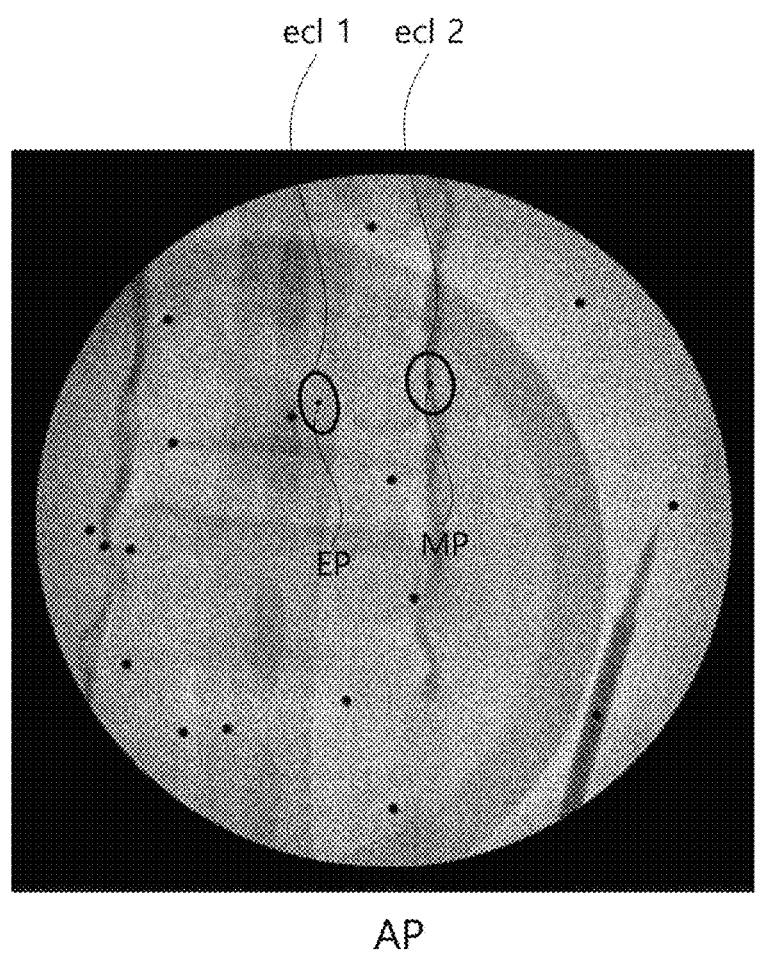
Figure 5B:
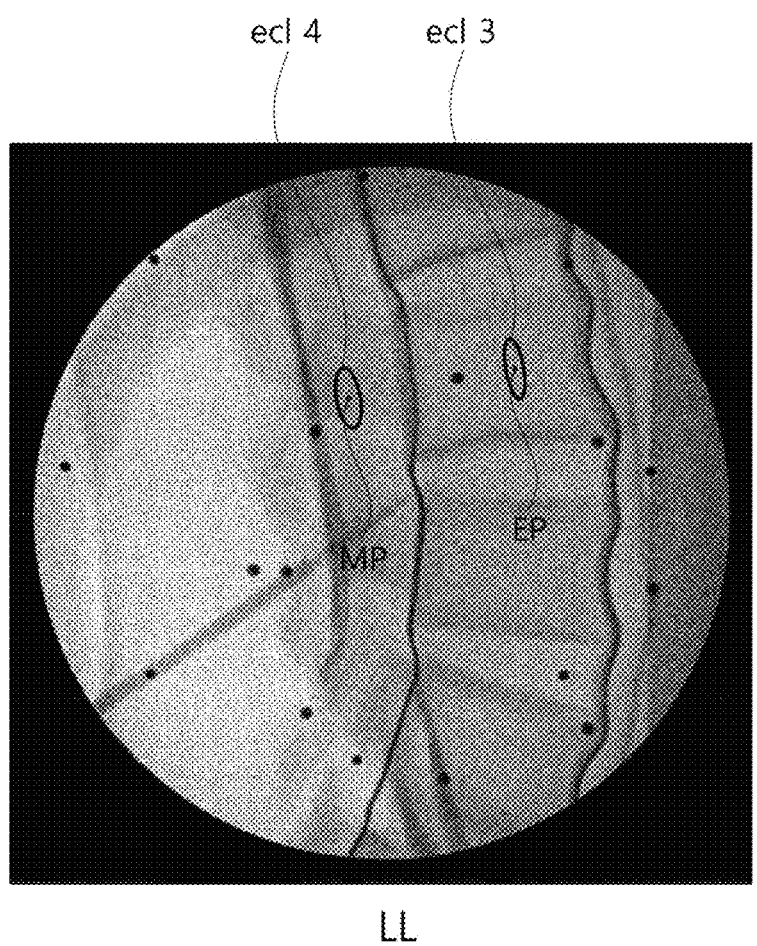

FIGS. 5A and 5B illustrate examples that the entry point and the insertion endpoint are marked on the AP image and the LL image according to an embodiment of the disclosure.

Referring to FIG. 5A, the left ellipse (hereinafter, referred to as a 'first ellipse') ecl1 indicates an insertion endpoint EP, and the right ellipse (hereinafter, referred to as a 'second ellipse') ecl2 indicates an entry point MP. Here, the reason why the ellipse is used is because the pedicle screw is inserted in a direction oblique to a direction of capturing the AP image and the diameter of the pedicle screw is represented, in which the first ellipse ecl1 indicates the end section of the pedicle screw, and the centers of the ellipses represent the insertion endpoint EP and the entry point MP, respectively.

Referring to FIG. 5B, the right ellipse (hereinafter, referred to as a 'third ellipse') ecl3 indicates the insertion endpoint EP, and the left ellipse (hereinafter, referred to as a 'fourth ellipse') ecl4 indicates the entry point MP. The entry point MP and the insertion endpoint EP shown in FIGS. 5A and 5B are located at places linked to each other.

Figure 6:
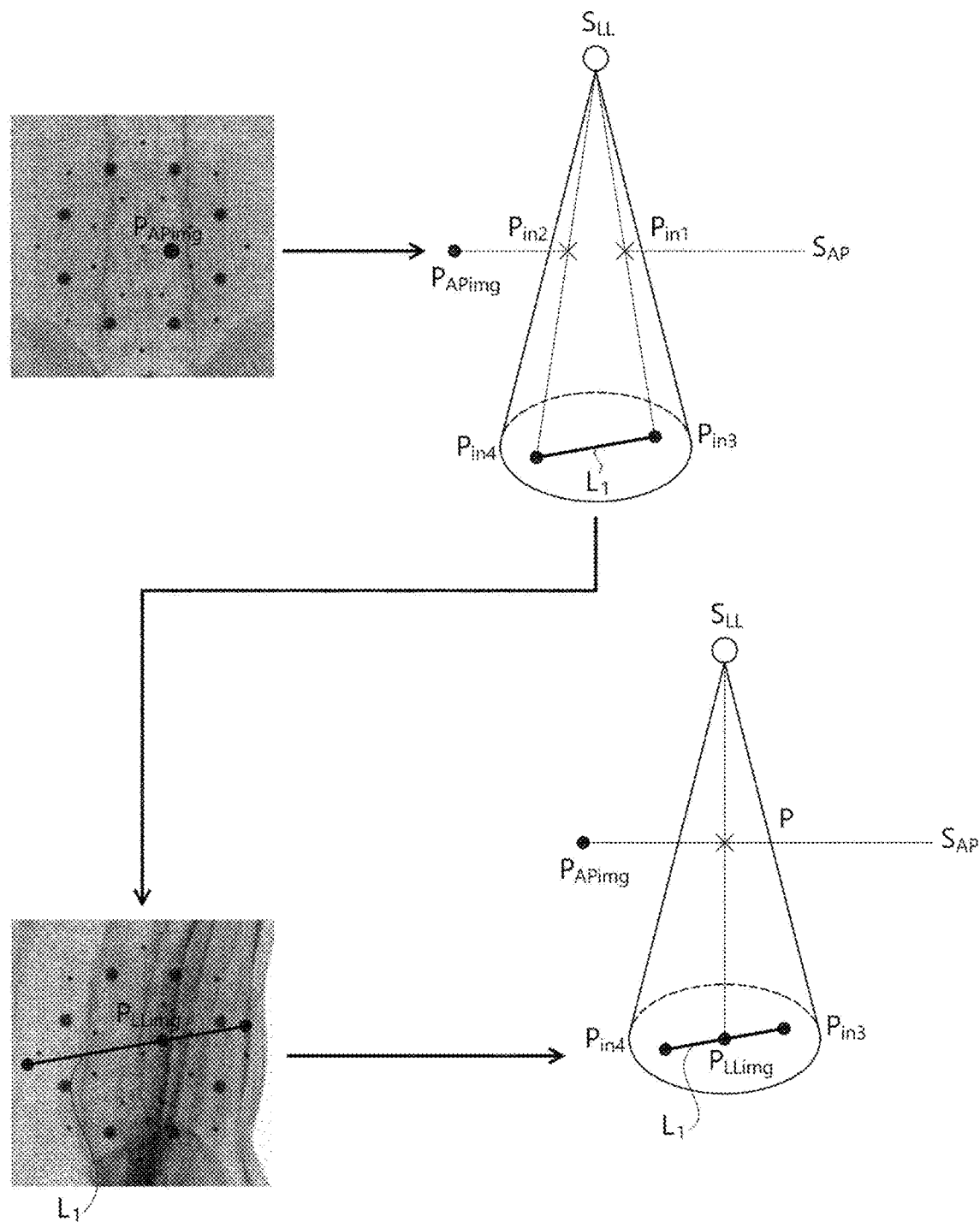

Referring to FIG. 6, the AP image and the LL image are obtained by capturing a patient's spine in a vertical direction. Therefore, a line extended from a certain point $P_{APimg}$ on the AP image, for example, the entry point in a reverse direction to the X-ray radiation direction can reach a source $S_{AP}$. Further, it is possible to obtain a line intersecting an area overlapping with the X-ray radiation direction when the LL image is captured, and it is also possible to obtain a first line $L_1$ by projecting the obtained line to the LL image. An entry point $P_{LLimg}$ on the LL image corresponding to the certain point $P_{APimg}$ on the AP image, for example, the entry point is one of pixels on the first line $L_1$. Therefore, if the location of the entry point on the AP image is changed, the location of the first line $L_1$ is changed and thus the location of the entry point on the LL image is also changed.

The insertion path provider 20 displays the AP image so that a surgical operator can select the entry point $P_{APimg}$, and displays the corresponding first line $L_1$ on the LL image so that the surgical operator can select the entry point $P_{LLimg}$ on the first line $L_1$, thereby allowing the surgical operator to input the entry points MP on the AP image and the LL image. Further, the insertion endpoint EP may be displayed besides the entry point MP by a method of recommending and displaying the entry point MP based on the CDSS assisting the surgical operator as described above.

Like this, the registration of pixels and coordinates between the AP image and the LL image described with reference to FIGS. 5A, 5B and 6 may be applied to all the pixels on the AP image and the LL image.

Figure 7A:
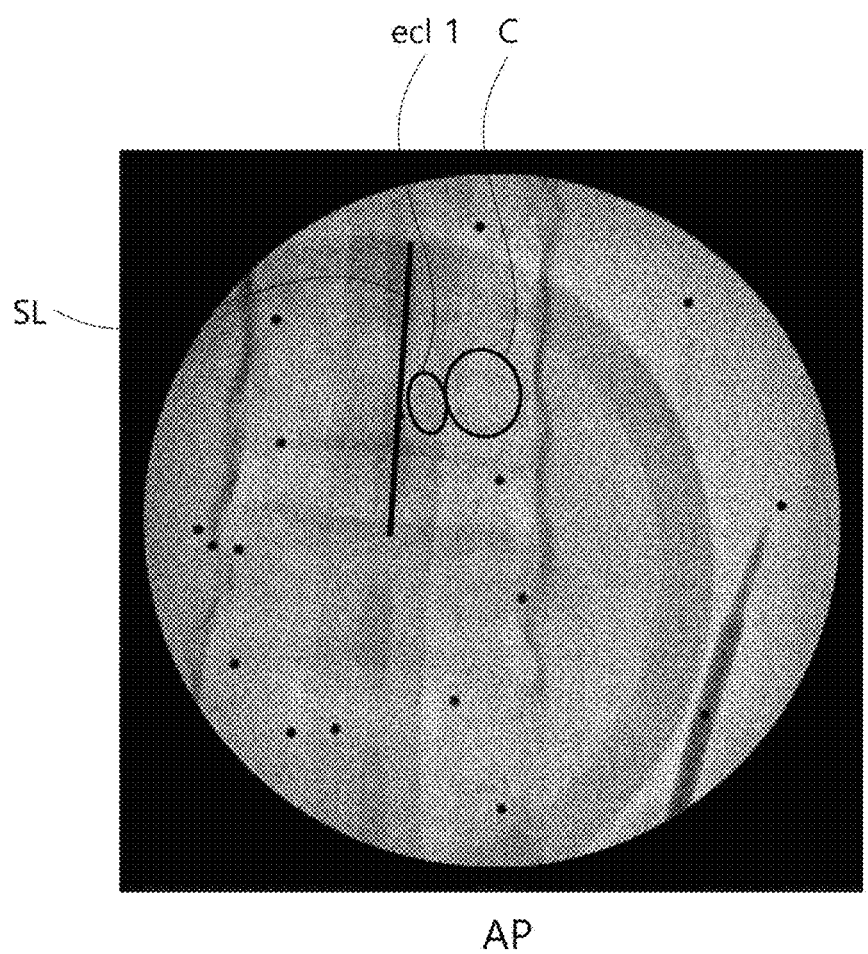
Figure 7B:
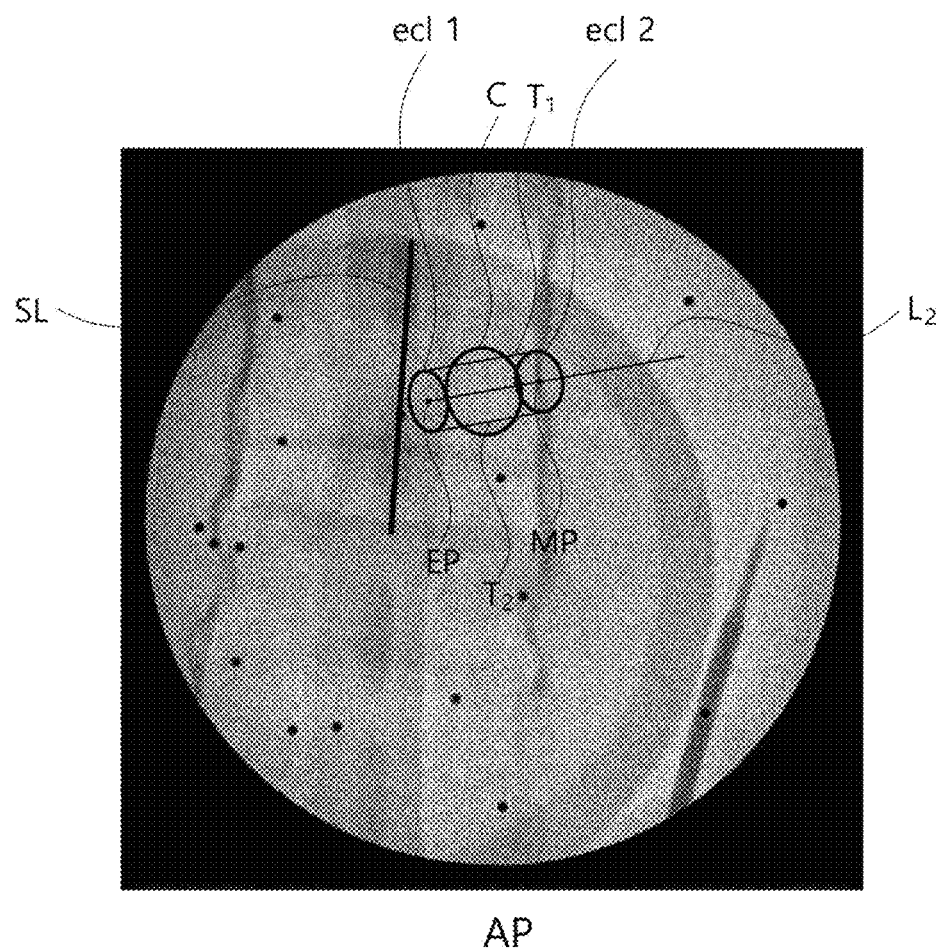

FIGS. 7A and 7B are schematic views for describing a process of determining a location of the insertion endpoint on the AP image.

In FIG. 7A, the line SL shown in a lengthwise direction indicates a spinous process of a spine, a circle C shown at the right side of the spinous process SL indicates the location of the pedicle. The insertion endpoint EP on the AP image is selected to be located between the circle C showing the pedicle and the spinous process SL, and the ellipse ecl1 centering on the insertion endpoint EP is also located between the circle C and the spinous process SL, thereby determining the location of the insertion endpoint EP and the shape of the ellipse.

Referring to FIG. 7B, the entry point MP may be selected on a second line $L_2$ connecting the first ellipse ecl1 and the circle C showing the pedicle. When two points at which the first ellipse ecl1 meets the major axis of the first ellipse ecl1 passing through the insertion endpoint EP and perpendicular to the second line $L_2$ are $EP_1$ and $EP_2$, and two points at which the second eclipse ecl2 meets the major axis of the second eclipse ecl2 passing through the entry point MP and perpendicular to the second line $L_2$ are $MP_1$ and $MP_2$, a line $T_1$ connecting the two points $EP_1$ and $MP_1$ and a line $T_2$ connecting the two points $EP_2$ and $MP_2$ are obtained.

The two points $(EP_1, EP_2)_{AP}$ obtained on the AP image and two points $(EP_1, EP_2)_{LL}$ obtainable on the LL image by the similar method are back projected along the X-ray path, thereby determining two intersection points $(EP_{1\_3d}, EP_{2\_3d})$ and calculating the spatial coordinates. Based on a distance between the two points $(EP_{1\_3d}, EP_{2\_3d})$ on the spatial coordinates obtained as above, it is possible to calculate the diameter of the pedicle screw.

When the insertion endpoint EP is moved, the first ellipse ecl1 is changed in shape, and thus the second ellipse ecl2 is also changed in shape.

Figure 8:
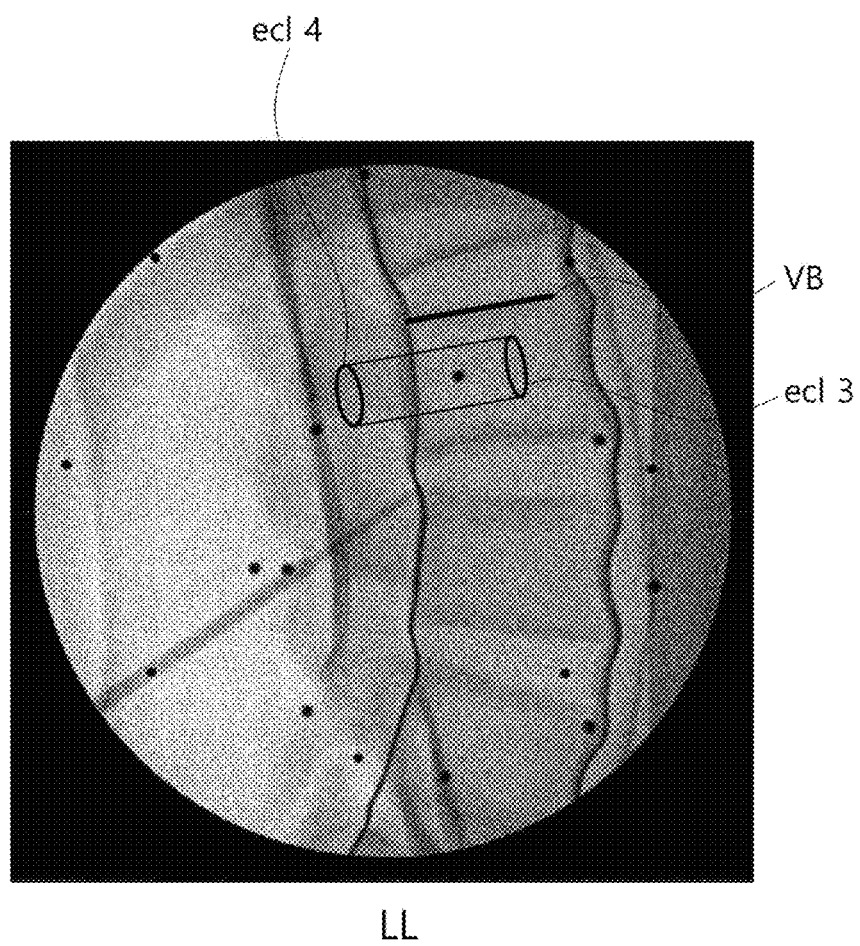

FIG. 8 is a schematic view for describing a process of determining a third ellipse ecl3 corresponding to the insertion endpoint and a fourth ellipse ecl4 corresponding to the entry point on the LL image.

The process of selecting the insertion endpoint and the entry point on the LL image in connection with the insertion endpoint and the entry point selected on the AP image has been described above. Likewise, the sizes of the third ellipse ecl3 and the fourth ellipse ecl4 shown in FIG. 8 may be determined by a method of registering the pixels of the first ellipse and the second ellipse (i.e., the method described with reference to FIG. 6). Therefore, when one of the first to fourth ellipses is changed in shape as its center is moved or a diameter is varied, the other three ellipses are also correspondingly changed in shape.

Even on the LL image, lines corresponding to the lines $T_1$ and $T_2$ may be determined by the same method as that on the AP image. On the LL image, the second line $L_2$ passing through the insertion endpoint EP and the entry point MP is positioned in parallel with a horizontal line VB shown on the image of the vertebral body.

Referring back to FIG. 3, next, the registrator 40 calculates the spatial coordinates of the entry point MP and the insertion endpoint EP based on the reference coordinate system (S3). Here, the reference coordinate system is established as the optical tracking device 30 recognizes reference optical markers installed in a medical space.

Figure 9:
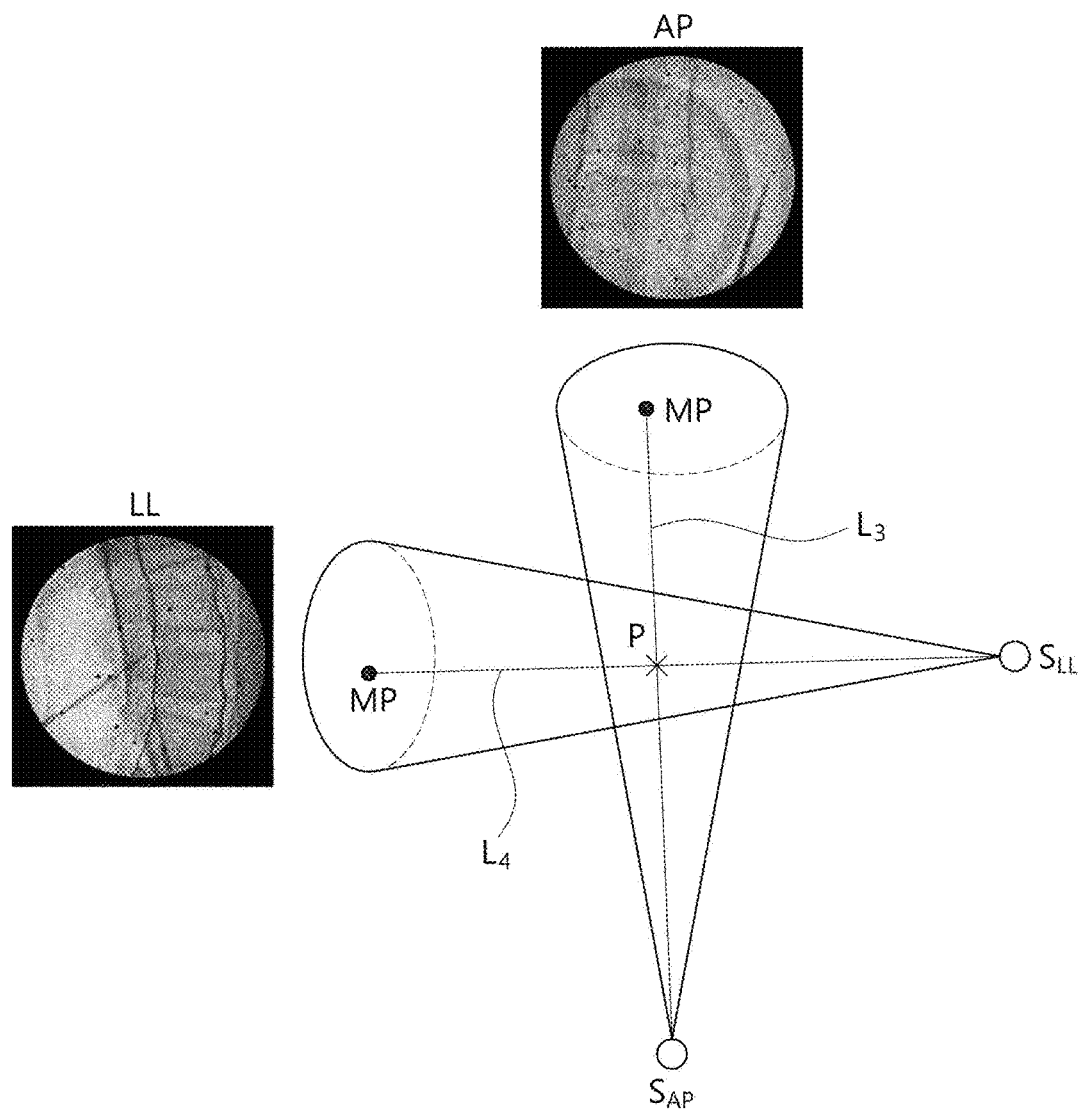

As shown in FIG. 9, the intersection P between the third line $L_3$ and the fourth line $L_4$, on which the entry point MP (or the insertion endpoint) shown on the AP image and the LL image orthogonal to each other is projected in a reverse direction to the X-ray radiation direction, may be calculated as the spatial coordinates registered to the entry point MP.

However, to obtain the spatial coordinates transformed by the method shown in FIG. 9, there is a need of information about a location of the source when the AP image and the LL image are captured, and a location of a detector plane where an image is formed. If it is impossible to know the location of the detector plane, an image may be generated by applying the warping algorithm to a plane on the X-ray radiation path where the spatial locations are known, as disclosed in Korean Patent Application No. 2019-0028592 of the present applicant, and replace the AP or LL image illustrated in FIG. 9.

The guider 50 determines the insertion position of the pedicle screw based on the spatial coordinates of the entry point and the insertion endpoint, and thus guides the probe to be inserted toward the entry point (S4).

In case of a medical robot, the medical robot moves to an appropriate location based on received spatial coordinates of the entry point and the insertion endpoint and locates a probe gripper for guiding a probe insertion direction according to insertion positions. It is well known in the art that the medical robot moves based on the given coordinates and sets the direction of the probe gripper mounted to the end effector to be oriented toward the insertion path connecting the entry point and the insertion endpoint, and therefore detailed descriptions will be omitted in the disclosure. Further, not the medical robot but a publicly known bridge-type surgical tool guider 50 or the like may also be controlled in a similar way.

The screw determiner 60 obtains the coordinates of the point, at which a probe end starts being in contact with the bone as the probe is inserted (hereinafter, referred to as a 'start point (SP)') (S5).

Figure 10A:
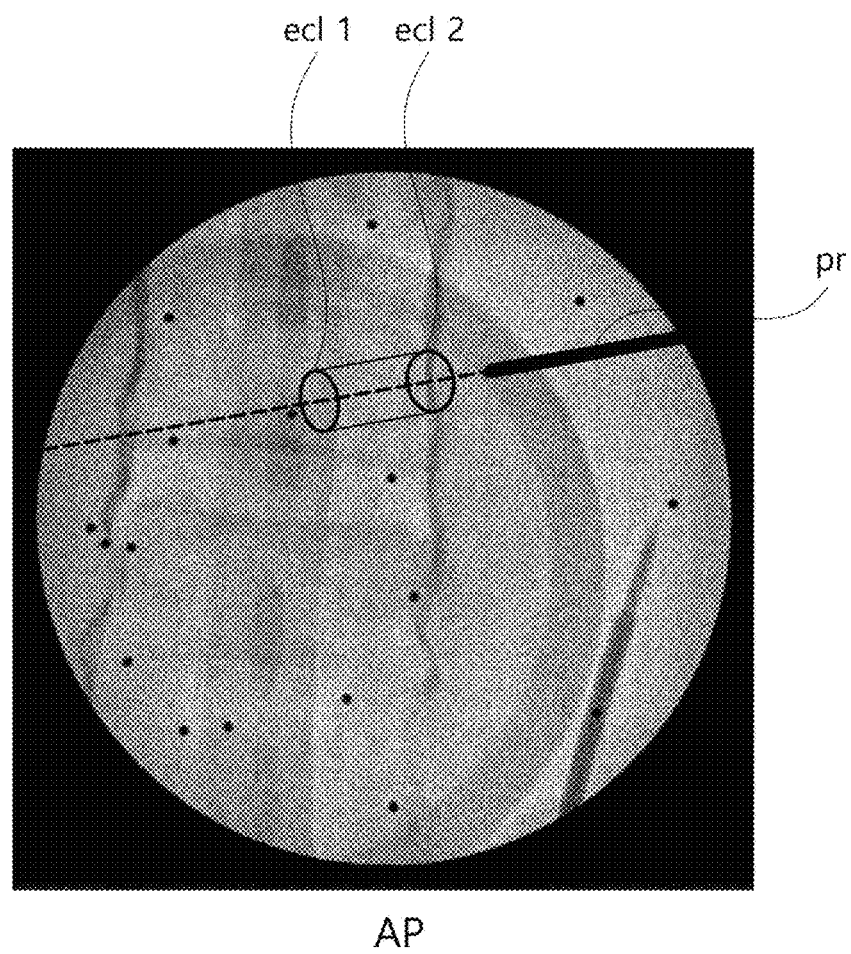
Figure 10B:
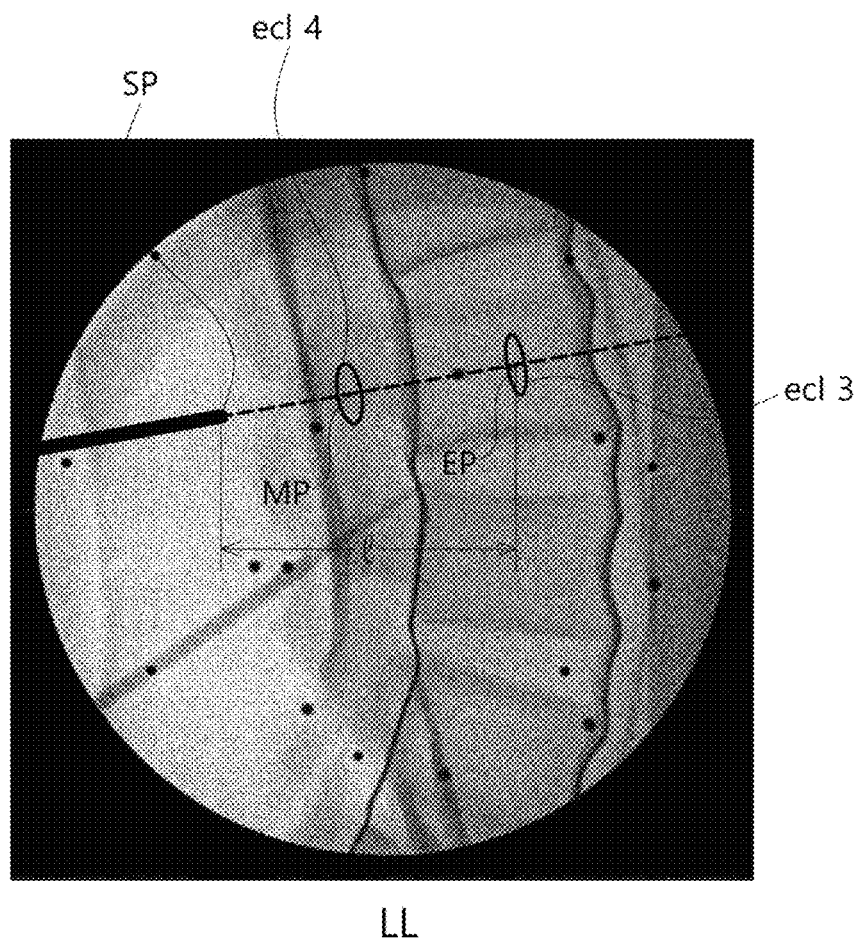

FIGS. 10A and 10B are the AP image and the LL image showing that the probe pr is inserted and is in contact with the start point.

The end SP of the inserted probe pr is varied depending on a probe insertion depth, but may be calculated as the spatial coordinates by means of the optical markers attached to the probe or the guider 50. The spatial coordinates of the probe end may, as shown in FIG. 9, may be registered to the locations on the AP image and the LL image along the X-ray radiation direction, and tracked in real time as shown in FIGS. 10A and 10B.

The screw determiner 60 determines the length condition of the pedicle screw by calculating the distance between the two points based on the coordinates of the start point SP and the coordinates of the insertion endpoint EP (S6). The length of the pedicle screw may be selected as a length equal to a 3D spatial distance between the coordinates of the start point and the coordinates of the insertion endpoint or a length longer by a predetermined length than the 3D spatial distance.

As described above, according to the disclosure, it is possible to determine the length of the screw by inserting the probe based on the C-arm image, but also the guide set for inserting the probe is usable in inserting the pedicle screw, thereby quickly and more accurately performing a surgical operation.

Although a few embodiments of the disclosure have been described, it is understood by a person having ordinary knowledge in the art to which the disclosure pertains that change or replacement can be made in the embodiments of the disclosure without departing from technical scope of the disclosure. Therefore, it is appreciated that the scope of the disclosure is within the technical concept defined in the appended claims and its equivalents.

The invention claimed is:

1. A system for planning pedicle screw fixation, comprising:
    a C-arm having an X-ray source and a detector disposed at opposite ends of a C-shaped frame, the C-arm being configured to capture a spinal image of a patient,
    wherein the system is configured to:
    acquire an anterior-posterior (AP) 2D image and a lateral-lateral (LL) 2D image of a spine of the patient through the C-arm;
    determine an entry point and an insertion endpoint of a pedicle screw on the AP 2D image and the LL 2D image;
    calculate spatial coordinates of the entry point and the insertion endpoint based on a reference coordinate system;
    determine an insertion orientation of the pedicle screw based on the spatial coordinates of the entry point and the insertion endpoint, and guide a probe to be inserted toward the entry point according to the insertion orientation;
    obtain coordinates of a start point at which the probe is to be in contact with a bone when the probe is inserted toward the entry point, and determine a length condition of the pedicle screw by calculating a distance between the spatial coordinates of the insertion endpoint and the coordinates of the start point; and
    determine a location of the entry point at a point on a line connecting the insertion endpoint and a center of a pedicle on the AP 2D image, and determine a location of the entry point at a point on a line extended from the insertion endpoint in parallel with a horizontal line of a vertebral body on the LL 2D image, such that, when the location of the entry point on the AP 2D image is changed, the location of the entry point on the LL 2D image is changed,
    wherein the spatial coordinate of the entry point is determined as an intersection of a first line and a second line, the first line (L1) is generated by back-projecting the entry point on the AP 2D image along an X-ray path, and the second line is generated by back-projecting the entry point on the LL 2D image along the X-ray path.

2. The system for planning pedicle screw fixation of claim 1, further comprising an optical tracking device configured to track a location of the probe to which an optical marker is connected, wherein the system is further configured to:
    determine a pixel on the AP 2D image and the LL 2D image to which the location of the probe is registered, and
    display a projected image of the probe on registered pixels.

3. The planning system for pedicle screw fixation of claim 1, further comprising a user interface allowing a surgical operator to select the entry point and the insertion endpoint on the AP 2D image and the LL 2D image.

4. The system for planning pedicle screw fixation of claim 1,
    wherein the entry point on the LL 2D image is determined as one on a line obtained by projecting a line extending from the entry point on the AP 2D image in a reverse direction to a X-ray radiation direction onto the LL 2D image.

5. The system for planning pedicle screw fixation of claim 4,
    further comprising an optical tracking device configured to track a location of the probe to which an optical marker is connected, wherein the system is further configured to determine a pixel on the AP 2D image and the LL 2D image to which the location of the probe is registered and display a projected image of the probe on registered pixels.

6. A method of planning pedicle screw fixation performed using a system including a C-arm, the method comprising:
   (a) obtaining an anterior-posterior (AP) 2D image and a lateral-lateral (LL) 2D image of a spine of a patient through the C-arm;
   (b) determining an entry point and an insertion endpoint of a pedicle screw on the AP 2D image and the LL 2D image acquired from the C-arm;
   (c) calculating spatial coordinates of the entry point and the insertion endpoint based on a reference coordinate system;
   (d) determining an insertion orientation of the pedicle screw based on the spatial coordinates of the entry point and the insertion endpoint to guide a probe to be inserted toward the entry point according to the insertion orientation;
   (e) obtaining coordinates of a start point at which the probe is to be in contact with a bone when the probe is inserted toward the entry point based on the reference coordinate system; and
   (f) determining a length condition of the pedicle screw by calculating a distance between the spatial coordinates of the insertion endpoint and the coordinates of the start point,
   wherein a location of the entry point is determined at a point on a line connecting the insertion endpoint and a center of a pedicle on the AP 2D image, and determining a location of the entry point at a point on a line extended from the insertion endpoint in parallel with a horizontal line of a vertebral body on the LL 2D image, such that, when the location of the entry point on the AP 2D image is changed, the location of the entry point on the LL 2D image is changed,
   wherein the spatial coordinate of the entry point is determined as an intersection of a first line and a second line, the first line (L1) is generated by back-projecting the entry point on the AP 2D image along an X-ray path, and the second line is generated by back-projecting the entry point on the LL 2D image along the X-ray path.

7. The method of planning pedicle screw fixation of claim 6, wherein the step (b) includes allowing a surgical operator to select the entry point and the insertion endpoint on the AP 2D image and the LL 2D image through a user interface.

8. The method of planning pedicle screw fixation of claim 6,
   wherein the entry point on the LL 2D image is determined as one on a line obtained by projecting a line extending from the entry point on the AP 2D image in a reverse direction to a X-ray radiation direction onto the LL 2D image.

9. The method of planning pedicle screw fixation of claim 8, wherein the step (b) includes allowing a surgical operator to select the entry point and the insertion endpoint on the C-arm 2D image through a user interface.

* * * * *